United States Patent
Sun et al.

(10) Patent No.: US 7,114,951 B2
(45) Date of Patent: Oct. 3, 2006

(54) METHOD AND SHAPED PRODUCT-FORMED FROM LOW TACK AND FLUORESCING POLYMERIZABLE DENTAL MATERIAL

(75) Inventors: Benjamin J. Sun, York, PA (US); Andrew M Lichkus, York, PA (US)

(73) Assignee: DENTSPLY International Inc., York, PA (US)

( * ) Notice: Subject to any disclaimer, the term of this patent is extended or adjusted under 35 U.S.C. 154(b) by 209 days.

(21) Appl. No.: 10/249,345

(22) Filed: Apr. 2, 2003

(65) Prior Publication Data

US 2003/0152888 A1 Aug. 14, 2003

Related U.S. Application Data

(63) Continuation-in-part of application No. 10/106,741, filed on Mar. 26, 2002, now abandoned, which is a continuation-in-part of application No. 09/682,440, filed on Sep. 4, 2001, now Pat. No. 6,592,369, which is a continuation-in-part of application No. 09/670,364, filed on Sep. 26, 2000, now abandoned, application No. 10/249,345, and a continuation-in-part of application No. 10/306,096, filed on Nov. 27, 2002, now Pat. No. 6,799,969, which is a continuation of application No. 09/670,364, filed on Sep. 26, 2000, now abandoned.

(60) Provisional application No. 60/237,523, filed on Oct. 4, 2000, provisional application No. 60/201,705, filed on May 3, 2000, provisional application No. 60/164,893, filed on Nov. 10, 1999.

(51) Int. Cl.
*A61C 13/00* (2006.01)

(52) U.S. Cl. ..................... 433/167
(58) Field of Classification Search .......... 433/6, 433/167, 199.1, 215, 215.1; 29/896.1, 896.11
See application file for complete search history.

(56) References Cited

U.S. PATENT DOCUMENTS

| | | | |
|---|---|---|---|
| 4,017,971 A | 4/1977 | Hazar | 32/2 |
| 4,094,067 A | 6/1978 | Hazar | 32/2 |
| 4,097,992 A | 7/1978 | Hazar | 32/2 |
| 4,133,110 A | 1/1979 | Bernstein et al. | 32/2 |
| 4,161,065 A | 7/1979 | Gigante | 32/2 |
| 4,175,322 A | 11/1979 | Tureaud | 433/171 |
| 4,247,287 A | 1/1981 | Gigante | 433/199 |
| 4,248,807 A | 2/1981 | Gigante | 264/18 |
| 4,259,074 A | 3/1981 | Link | 433/214 |
| 4,345,900 A | 8/1982 | Katz et al. | 433/171 |
| 4,375,966 A | 3/1983 | Freeman | 433/37 |
| 4,457,818 A | 7/1984 | Denyer et al. | 204/159 |
| 4,468,202 A | 8/1984 | Cohen | 433/199 |
| 4,543,063 A | 9/1985 | Cohen | 433/175 |
| 4,551,098 A | 11/1985 | Blair | 433/171 |
| 4,595,598 A * | 6/1986 | De Luca et al. | 433/10 |
| 4,609,351 A | 9/1986 | Blair | 433/55 |
| 4,705,476 A | 11/1987 | Blair | 433/171 |
| 4,721,735 A | 1/1988 | Bennett et al. | 522/71 |
| 4,813,875 A | 3/1989 | Hare | 433/214 |
| 4,892,478 A * | 1/1990 | Tateosian et al. | 433/6 |
| 4,978,298 A | 12/1990 | Eliasz | 433/213 |
| 5,063,255 A | 11/1991 | Hasegawa et al. | 522/96 |
| 5,177,120 A | 1/1993 | Hare et al. | 433/37 |
| 5,213,498 A | 5/1993 | Pelerin | 433/37 |
| 5,269,682 A * | 12/1993 | Kesling | 433/24 |
| 5,304,063 A | 4/1994 | Ginsburg | 433/199 |
| 5,403,186 A | 4/1995 | Ginsburg | 433/199 |
| 5,513,988 A * | 5/1996 | Jeffer et al. | 433/168.1 |
| 5,591,786 A | 1/1997 | Oxman et al. | 533/109 |
| 5,635,545 A | 6/1997 | Oxman et al. | 523/115 |
| 5,711,668 A | 1/1998 | Huestis | 433/167 |
| 5,952,400 A * | 9/1999 | Hosoi et al. | 523/120 |
| 5,993,208 A | 11/1999 | Jonjic | 433/50 |
| 6,031,015 A | 2/2000 | Ritter et al. | 522/77 |
| 6,057,383 A | 5/2000 | Volkel et al. | 523/116 |
| 6,244,864 B1 | 6/2001 | Fujiwara et al. | 433/71 |
| 6,808,659 B1 * | 10/2004 | Schulman et al. | 264/16 |

FOREIGN PATENT DOCUMENTS

| | | |
|---|---|---|
| EP | 0 630 640 | 12/1994 |
| EP | 813 856 | 12/1997 |
| EP | 1 042 994 | 10/2000 |
| GB | 2 225 333 | 5/1990 |

OTHER PUBLICATIONS

Moszner N. et al; "Synthesis Characterization and Polymerization of Waxy Monomers", 1997.

* cited by examiner

*Primary Examiner*—Todd E. Manahan
(74) *Attorney, Agent, or Firm*—Daniel W. Sullivan; James B. Bieber; Douglas J. Hura

(57) ABSTRACT

The invention provides a method of making a dental appliance by shaping a low ball tack polymerizable material. By including fluorescing agent the surfaces of dental appliances are visually identifiable.

4 Claims, No Drawings

METHOD AND SHAPED PRODUCT-FORMED FROM LOW TACK AND FLUORESCING POLYMERIZABLE DENTAL MATERIAL

CROSS REFERENCE TO RELATED APPLICATIONS

This application is a continuation-in-part of U.S. patent application Ser. No. 10/106,741 filed Mar. 26, 2002 now abandoned which is a continuation-in-part of U.S. patent application Ser. No. 09/682,440 filed Sep. 4, 2001 now U.S. Pat. No. 6,592,369 which is a continuation-in-part of U.S. patent application Ser. No. 09/670,364 filed Sep. 26, 2000, (abandoned). This application is a continuation-in-part of U.S. patent application Ser. No. 10/306,096 filed Nov. 27, 2002 now U.S. Pat. No. 6,799,969 which is a continuation of U.S. patent application Ser. No. 09/670,364 filed Sep. 26, 2000, (abandoned). The benefit is claimed of U.S. provisional patent application Ser. No. 60/237,523 filed Oct. 4, 2000, U.S. Provisional patent application Ser. No. 60/201,705 filed May 3, 2000, and U.S. Provisional Patent application Ser. No. 60/164,893 filed Nov. 10, 1999.

DETAILED DESCRIPTION

The invention relates to dental appliances and methods for making them. The dental appliance has an outer surface and fluorescing agent. The portion of the dental appliance having the outer surface is preferably formed by shaping a low ball tack polymerizable material. The dental appliance preferably includes high strength dental polymeric material. "Low ball tack polymerizable material" as used herein refers to polymerizable material having a ball tack of more than 1 inch at 37° C. when tested according to ASTM D3121-94 (modified) As used herein ASTM D3121-94 (modified) means ASTM D3121-94 modified by: 1) reducing the ball diameter to ¼ inch from 7/16 inch, and 2) starting the ball one inch from the bottom end of the ramp, thus reducing the length of ramp used (to accelerate the ball) to 1.0 inch from 6.5 inches. Preferably low ball tack polymerizable material has a ball tack in order of increasing preference of more than 2, 4, 6, 8, 10, 12 or 14 inches at 37° C. when tested according to ASTM D3121-94 (modified). Preferably low ball tack polymerizable material has a ball tack in order of increasing preference of more than 1, 2, 4, 6, 8 or 10 inch(es) at 45° C. when tested according to ASTM D3121-94 (modified). Preferably low ball tack polymerizable material has a ball tack in order of increasing preference of more than 1, 2, 4, 6, 8, 10, 12, 14, 16 or 18 inch(es) at 23° C. when tested according to ASTM D3121-94 (modified).

"High strength dental polymeric material" as used herein refers to material having a polymeric matrix having a flexural modulus of at least 250,000 psi and a flexural strength of at least 5,000 psi. Optionally, high strength dental polymeric material includes reinforcing filler. However, the polymeric matrix alone (without any reinforcing filler) has a flexural modulus of at least 250,000 psi and a flexural strength of at least 5,000 psi. Preferably high strength dental polymeric material has a polymeric matrix having a flexural modulus of at least 300,000 psi and a flexural strength of at least 7,000 psi, and an un-notched impact strength of at least 2 foot-pounds/inch$^2$. More preferably high strength dental polymeric material in order of increasing preference has a polymeric matrix having a flexural modulus of at least 350,000 psi and a flexural strength of at least 12,000 psi, and an un-notched impact strength of at least 3.0 foot-pounds/inch. High strength dental polymeric material is preferably formed into dental products including full dentures, partial dentures, denture relines, night guards, crowns and bridges by polymerization of wax-like polymerizable dental material.

"Flexural strength, and flexural modulus" as used herein refers to results of testing according to ASTM D790 (1997). "Notched impact strength" as used herein is also referred to as "notched Izod impact resistance" and refers to results of testing according to ASTM D256 (1997). "Un-notched impact strength" as used herein refers to results of testing according to ASTM D4812 (1993).

A preferred embodiment of the invention provides dental appliances and methods using fluorescing agents to identify the bond forming ability of surfaces. The fluorescing agent(s) are included in the dental appliance to make them visually identifiable. For example as a material requiring specific processing, such as application of a particular bonding agent for bonding thereto.

Visually identifiable polymerizable dental material is useful for formation of dental products of the invention, which include full dentures, partial dentures, denture liners, denture repairs, retainers, orthodontic components, orthodontic appliances, oral orthopedic appliances, temporary dentures, and temporary partial dentures, trays and baseplates, and othotics, such as night guards, splints, stents.

Exemplary additional fluorescing agents that are suitable for use in accordance with the invention are coumarin derivatives, phthalimide derivatives, fluoranthrene derivatives, perylene derivatives, xanthene derivatives, thioxanthene derivatives, pyrano-benzopyran-2,5-dione derivatives, pyrano-quinoline-2,5 derivatives, pyrazole quinoxlaine derivatives, 2-pyrano-isoquinoline-3,6-dione derivatives, benzimidazo-benz-isoquinoline-7-one derivatives, acridine derivatives and mixtures thereof as disclosed in U.S. Pat. No. 5,102,461. A preferred fluorescing agent useful for formation of dental products of the invention is a blend of zinc oxide/magnesium oxide and dihydroxy terepthalate acid ester (sold by Hoechst Celanese as Lumilux Blue LX #52055). This fluorescing agent absorbs in the 320–400 nm range and emits visable blue light. Fluorescein has an absorption maximum of 494 nm and an emission of 520 nm.) Compositions for use in methods in accordance with the invention may further include fillers, pigments, stabilizers, plasticizers and fibers. Optionally, polymerizable dental compositions for use in methods in accordance with the invention include from about 2 to about 95 percent by weight filler particles. Preferably, these compositions include from about 10 to about 85 percent by weight filler. The fillers preferably include both organic and inorganic particulate fillers to further reduce polymerization shrinkage, improve wear resistance. Nanocomposites and ceramers may be formed from these composites.

Catalysts known in the art may be used to accelerate the formation of pre-oligomer and ethylenically unsaturated monomer, for examples, tertiary amines and metal salts, e.g. stannous octoate and in particular dibutyl tin dilaurate. Preferred stabilizers used in this invention are butylated hydroxytoluene (BHT) and the methyl ether of hydroquinone (MEHQ). Polymerizable dental material may include one or more initiating systems to cause them to harden promptly. Light curable polymerizable dental materials preferably include a light sensitizer, for example camphorquinone, Lucirin TPO, or methyl benzoin which causes polymerization to be initiated upon exposure to activating wavelengths of light; and/or a reducing compound, for example tertiary amine. A room temperature or heat activating catalyst system is preferably included in the polymerizable dental material of the invention. Preferably included is a peroxide capable of producing free radicals when activated by a reducing agent at room temperature or by heating. Preferred peroxides include benzyl peroxide and lauroyl peroxide.

In the following examples, unless otherwise indicated, all parts and percentages are by weight; Lucirin TPO refers to 2,4,6-trimethylbenzoyldiphenylphosphine oxide made by BASF, and the visible light curing unit used was an ECLIPSE VLC visible light curing and processing unit providing about 30 milliwatts/cm$^2$ of light having wavelengths of from 350 to 450 nm.

Preparation 1

Preparation of Monomer

A reaction flask was charged with 700 grams of 1,6-diisocyanatohexane and heated to about 70° C. under a positive nitrogen pressure. To this reactor were added 1027 grams of 2-hydroxyethyl methacrylate, 0.75 gram of catalyst dibutyltin dilaurate and 4.5 grams of butylated hydroxy toluene (BHT). The addition was slow and under dry nitrogen flow over a period of two hours. The temperature of the reaction mixture was maintained between 70° C. and 90° C. for another two hours and followed by the addition of 8.5 grams of purified water. One hour later, the reaction product was discharged as clear liquid into plastic containers and cooled to form a white solid and stored in a dry atmosphere.

EXAMPLE 1A

Preparation of Oligomer

A reactor was charged with 1176 grams of trimethyl-1,6-diisocyanatohexane (5.59 mol) and 1064 grams of bisphenol A propoxylate (3.09 mol) under dry nitrogen flow and heated to about 65° C. under a positive nitrogen pressure. To this reaction mixture, 10 drops of catalyst dibutyltin dilaurate were added. The temperature of the reaction mixture was maintained between 65° C. and 140° C. for about 70 minutes and followed by additional 10 drops of catalyst dibutyltin dilaurate. A viscous paste-like isocyanate end-capped intermediate product was formed and stirred for 100 minutes. To this intermediate product, 662 grams (5.09 mol) of 2-hydroxyethyl methacrylate, 7.0 grams of BHT as an inhibitor were added over a period of 70 minutes while the reaction temperature was maintained between 68° C. and 90° C. After about five hours stirring under 70° C., the heat was turned off, and oligomer was collected from the reactor as semi-translucent flexible solid and stored in a dry atmosphere.

EXAMPLE 1B

Preparation of Oligomer with Fluorescing Agent

A reactor is charged with 1176 grams of trimethyl-1,6-diisocyanatohexane (5.59 mol) and 1064 grams of bisphenol A propoxylate (3.09 mol) under dry nitrogen flow and heated to about 65° C. under a positive nitrogen pressure. To this reaction mixture, 10 drops of catalyst dibutyltin dilaurate is added. The temperature of the reaction mixture was maintained between 65° C. and 140° C. for about 70 minutes and followed by additional 10 drops of catalyst dibutyltin dilaurate. A viscous paste-like isocyanate end-capped intermediate product is formed and stirred for 100 minutes. To this intermediate product, 662 grams (5.09 mol) of 2-hydroxyethyl methacrylate, 7.0 grams of BHT as an inhibitor and 40 mg of fluorescing agent is added over a period of 70 minutes while the reaction temperature was maintained between 68° C. and 90° C. After about five hours stirring under 70° C., the heat was turned off, and oligomer was collected from the reactor as semi-translucent flexible solid and stored in a dry atmosphere.

The fluorescing agent is a blend of 30 mg of a zinc oxide/magnesium oxide complex, and 10 mg of dihydroxy terepthalate acid ester. The zinc oxide/magnesium oxide complex is made by blending and stirring 62.24% ZnO (USP), 20.75% ZnO (Kadox 91), 16.18% magnesium carbonate, 0.62% lithium sulfate, and 0.21% sulfur, sublimed powder, (and this composition is sometimes called 115 Phosphor). The dihydroxy terephthalate acid ester sold by Hoechst Celanese as Lumilux Blue LX #52055, (and sometimes called FLU-L-BLU).

EXAMPLE 2

Preparation of Polymerizable Denture Base Plate Material

A light curable polymerizable denture base plate material was prepared by stirring at 85° C. a liquid of 98.0 grams of TBDMA oligomer of Example 1A, 0.35 gram of 2,4,6-trimethylbenzoyldiphenylphosphine oxide, (Lucirin TPO made by BASF), 1.5 gram of solution containing 8.3% camphorquinone (CQ), 25% ethyl 4-dimethylaminobenzoate (EDAB) and 66.7% 1,6-hexanediol dimethacrylate (HDDMA), 0.1 gram of red acetate fibers and 0.05 gram of pigment. This polymerizable denture base plate material has a ball tack of more than 10 inches at each of 23, 37° C., and 45° C., when tested according to ASTM D3121-94 (Modified).

EXAMPLE 2A

Preparation of Polymerizable Denture Base Plate Material

A light curable polymerizable denture base plate material was prepared by stirring at 85° C. a liquid of 98.0 grams of TBDMA oligomer of Example 1B, 0.35 gram of 2,4,6-trimethylbenzoyldiphenylphosphine oxide, (Lucirin TPO made by BASF), 1.5 gram of solution containing 8.3% camphorquinone (CQ), 25% ethyl 4-dimethylaminobenzoate (EDAB) and 66.7% 1,6-hexanediol dimethacrylate (HDDMA), 0.1 gram of red acetate fibers and 0.05 gram of pigment. This polymerizable denture base plate material has a ball tack of more than 10 inches at each of 23, 37° C., and 45° C., when tested according to ASTM D3121-94 (Modified)

EXAMPLE 3

Preparation of Polymerizable Wax-like Denture Contour Material

A light curable wax-like polymerizable dental material was prepared by stirring at 85° C. a liquid mixture of 50.5 grams of oligomer of Example 1A, 45.0 grams of monomer of Preparation 1 and 4.0 grams of stearyl acrylate from Sartomer. To this mixture were added 0.35 gram of 2,4,6-trimethylbenzoyldiphenylphosphine oxide (Lucirin TPO), 0.1 gram of red acetate fibers and 0.05 gram of pigment concentrates. The polymerizable wax-like material formed becomes flowable at 65 to 68° C.

EXAMPLE 4

Preparation of Polymerizable Denture Set-up Material

A light curable polymerizable material was prepared by stirring at 85° C. a liquid mixture of 84.5 grams of oligomer of Example 1A and 15.0 grams of monomer of Preparation 1. To this mixture, 0.35 gram of 2,4,6-trimethylbenzoyl-diphenylphosphine oxide (Lucirin TPO), 0.1 gram of red acetate fibers and 0.05 gram of pigment were added.

EXAMPLE 5

Preparation of a Denture without Forming a Mold Cavity of a Denture Base.

A plaster cast of a patient's mouth is coated with a release agent (e.g., AL-COTE and ISOLANT sold by Dentsply International Inc. or TEFLON fluoropolymer solution such as KRYTOX from Dupont) and heated to 55° C. in an incubator. An arch-shaped baseplate resin containing 14 grams of the product of Example 2 is applied and shaped onto the warm cast. The resin is shaped and flowed to fully cover the cast, using finger pressure and trimming to form a baseplate. The baseplate is cured for 10 minutes in the visible light curing unit. A sufficient quantity of the product of Example 6 is formed into a rope. The rope is applied to the baseplate. Then artificial teeth are pressed into the rope with the thickness of the rope adapted to adequately cover the appropriate surfaces of the teeth to provide support. Melted product of Example 3 from an about 87° C. wax pot is applied by using an electric spatula between the teeth and the baseplate to fully embed teeth and to flow into fissures between teeth and to smooth the outer surface of the denture. Hot air from a small nozzle hot air gun may also be applied to let the product of Example 3 flow into fissures between teeth and smooth the outer surface of the denture. The lingual and buccal surfaces of the denture are contoured, trimmed and carved using a spatula. The denture is placed in a patient's mouth for try-in at a dental office and tooth positions are adjusted. The denture back is fitted to the cast and the TRIAD Air Barrier Coating is painted on the denture. Then a model release agent (MRA) sold by Dentsply International Inc. is applied to around posterior teeth and supporting resin. A strip of TRIAD gel is applied on surface between teeth and supporting resin to form a continuous circle and cured in a visible light curing unit for 10 minutes, followed by post curing for 8 hours of gradually cooling to 23° C. When cured, the denture is washed with water to remove all traces of Air Barrier Coating. The denture is then finished and polished.

Relining the Denture. The portion of the denture formed from the product of Example 2 (Polymerizable Denture Base Plate Material) fluoresces and thus is readily visually identifiable when exposed to black light. TRIAD bonding agent is applied to the fluorescing surface, and exposed to light from a curing light for 2 minutes to form a prepared surface. LUCISOF (or PERMASOFT) reline material is then applied to the prepared surface to form a relined denture.

EXAMPLE 6

Preparation of a Night Guard Without Forming a Mold Cavity of a Night Guard.

A plaster cast of a patient's teeth is coated with a release agent and warmed to 50° C. in an oven. 14 grams of the product composition of Example 2 is applied over the warmed cast. The composition is shaped using finger pressure and trimming to form a night guard, which hardens when cooling to room temperature. When adapting resin to articulated models, mold release agent is applied to the incisal and occlusal surface of the opposing model. After the night guard is examined and adjusted to fit articulator, TRAID Air Barrier Coating is painted on the night guard on the cast and cured for 10 minutes. The clear night guard is then washed with water to remove all traces of Air Barrier Coating. The night guard is then finished and polished.

Relining the Night Guard The portion of the denture formed from the product of Example 2 (Polymerizable Denture Base Plate Material) fluoresces and thus is readily visually identifiable when exposed to black light. Triad bonding agent is applied to the fluorescing surface, and exposed to light from a curing light for 2 minutes to form a prepared surface. LuciSof (or PermaSoft) reline material is then applied to the prepared surface to form a relined night guard.

It should be understood that while the present invention has been described in considerable detail with respect to certain specific embodiments thereof, it should not be considered limited to such embodiments but may be used in other ways without departure from the spirit of the invention and the scope of the appended claims.

The invention claimed is:

1. A method of relining a dental appliance, comprising:
providing a dental appliance having an outer surface formed from a polymerizable material, and said material comprising fluorescing agent, and said fluorescing agent being visually perceptible upon being exposed to light having a wavelength in the range of 320 to 400 nm,
irradiating said outer surface with light having a wavelength in the range of 320 to 400 nm to visually identify said outer surface,
applying a bonding agent to said outer surface to form a prepared surface that will bond to a reline material, and
applying a reline material to said prepared surface.

2. The method of claim 1 wherein said outer surface is formed by shaping a low ball tack polymerizable material.

3. A method of relining a dental appliance, comprising:
providing a dental appliance having an outer surface formed from a polymerizable material, and said material comprising fluorescing agent, and said fluorescing agent being visually perceptible upon being exposed to light having a wavelength in the range of 320 to 400 nm, and said dental appliance being selected from the group consisting of: night guard, splint, and orthodontic retainer,
irradiating said outer surface with light having a wavelength in the range of 320 to 400 nm to visually identify said outer surface,
applying a bonding agent to said outer surface to form a prepared surface that will bond to a reline material, and
applying a reline material to said prepared surface.

4. The method of claim 3 wherein said outer surface is formed by shaping a low ball tack polymerizable material.

* * * * *